(12) United States Patent
Andrés-Gil et al.

(10) Patent No.: US 6,511,976 B1
(45) Date of Patent: Jan. 28, 2003

(54) HALOGEN SUBSTITUTED TETRACYCLIC TETRAHYDROFURAN DERIVATIVES

(75) Inventors: José Ignacio Andrés-Gil, Madrid (ES); Francisco Javier Fernández-Gadea, Toledo (ES); Pilar Gil-Lopetegui, Toledo (ES); Adolfo Díaz-Martinez, Madrid (ES)

(73) Assignee: Jannsen Pharmaceutica, N.V. (BE)

( * ) Notice: Subject to any disclaimer, the term of this patent is extended or adjusted under 35 U.S.C. 154(b) by 0 days.

(21) Appl. No.: 09/529,252

(22) PCT Filed: Oct. 6, 1998

(86) PCT No.: PCT/EP98/06352

§ 371 (c)(1),
(2), (4) Date: Apr. 6, 2000

(87) PCT Pub. No.: WO99/19317

PCT Pub. Date: Apr. 22, 1999

(30) Foreign Application Priority Data

Oct. 10, 1997 (EP) .............................. 97203154

(51) Int. Cl.[7] .................. A61K 31/497; A61K 31/4523; A61K 31/5377; C07D 405/06; C07D 413/06
(52) U.S. Cl. .............................. 514/232.8; 514/254.11; 514/321; 514/414; 544/109; 544/375; 546/196; 546/197; 548/454; 548/525; 548/526
(58) Field of Search ........................ 514/232.8, 254.11, 514/321, 414, 422; 544/109, 375, 378; 546/196, 197; 548/454, 525, 526

(56) References Cited

FOREIGN PATENT DOCUMENTS

| HU | 99/02901 | 5/2000 |
|---|---|---|
| WO | WO 96/14320 | 5/1996 |
| WO | WO 96/14321 | 5/1996 |
| WO | WO 97/38991 | 10/1997 |
| WO | WO 98/08502 | 5/1998 |

OTHER PUBLICATIONS

I. Monkovic et al., "Substituted Tetrahydrofurfurylamines as potential antidepressants", J.Med Chem, 1973, vol. 16, No. 4, pp. 403–405.

Primary Examiner—T. A. Solola
(74) Attorney, Agent, or Firm—Mary Appollina

(57) ABSTRACT

This invention concerns the compounds of formula (I),

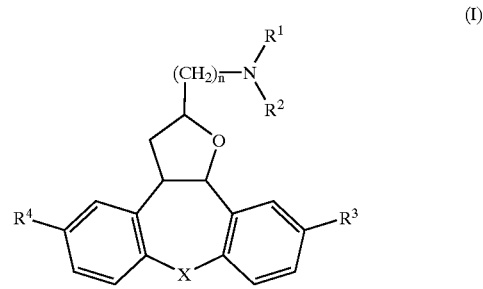

the N-oxide forms, the pharmaceutically acceptable addition salts and the stereochemically isomeric forms thereof, wherein n is zero, 1, 2, 3, 4, 5 or 6; X is $CH_2$ or O; $R^1$ and $R^2$ each independently are hydrogen, $C_{1-6}$alkyl, $C_{1-6}$alkylcarbonyl, halomethylcarbonyl or $C_{1-6}$alkyl substituted with hydroxy, $C_{1-6}$alkyloxy, carboxyl, $C_{1-6}$alkylcarbonyloxy, $C_{1-6}$alkyloxycarbonyl or aryl; or $R^1$ and $R^2$ taken together with the nitrogen atom to which they are attached may form a morpholinyl ring or an optionally substituted heterocycle; $R^3$ and $R^4$ are both halogen; or $R^3$ is halogen and $R^4$ is hydrogen; or $R^3$ is hydrogen and $R^4$ is halogen; and aryl is phenyl or phenyl substituted with 1, 2 or 3 substituents selected from halo, hydroxy, $C_{1-6}$alkyl and halomethyl. The compounds of formula (I) may be used as therapeutic agents.

9 Claims, No Drawings

HALOGEN SUBSTITUTED TETRACYCLIC TETRAHYDROFURAN DERIVATIVES

CROSS REFERENCE TO RELATED APPLICATIONS

This application is a National Stage application under 35 U.S.C. §371 of PCT/EP98/06352 filed Oct. 6, 1998.

This invention concerns halogen substituted tetracyclic tetrahydrofuran derivatives having antipsychotic, cardiovascular and gastrokinetic activity and their preparations; it further relates to compositions comprising them, as well as their use as a medicine.

WO 97/38991, published on Oct. 23, 1997, discloses tetracyclic tetrahydrofuran derivatives. WO 96/14320 and WO 96/14321 both disclose isoxazolidine containing tetracyclic derivatives, all having antipsychotic, cardiovascular and gastrokinetic activity.

An article by Monkovic et al. (J. Med. Chem. (1973), 16(4), p. 403–407) describes the synthesis of (±)-3,3a,8,12b-tetrahydro-N-methyl-2H-dibenzo[3,4:6,7]-cyclohepta-[1,2-b]furan-2-methanamine oxalic acid. Said compound was synthesized as potential antidepressant; however, it was found that this particular tetrahydrofurfurylamine derivative was inactive as antidepressant at a dose of 300 mg/kg.

The present compounds differ structurally from the art-known compounds by their specific substitution pattern on the dibenzoazepine ring and the presence of a tetrahydrofuran ring instead of an isoxazolidine ring, and are further distinguished by valuable pharmacological and physicochemical properties.

This invention concerns compounds of formula (I)

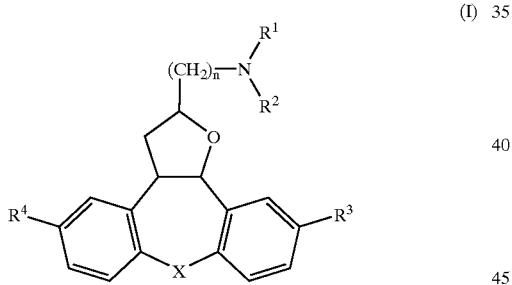

(I)

the N-oxide forms, the pharmaceutically acceptable addition salts and the stereochemically isomeric forms thereof, wherein:

n is zero, 1, 2, 3, 4, 5 or 6;

X is $CH_2$ or O;

$R^1$ and $R^2$ each independently are hydrogen, $C_{1-6}$alkyl, $C_{1-6}$alkylcarbonyl, halomethyl-carbonyl or $C_{1-6}$alkyl substituted with hydroxy, $C_{1-6}$alkyloxy, carboxyl, $C_{1-6}$alkyl-carbonyloxy, $C_{1-6}$alkyloxycarbonyl or aryl; or $R^1$ and $R^2$ taken together with the nitrogen atom to which they are attached may form a morpholinyl ring or a radical of formula:

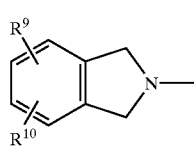

(a)

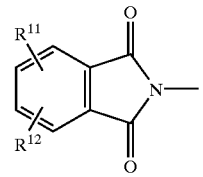

(b)

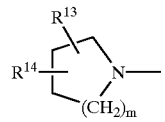

(c)

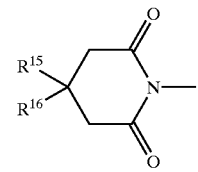

(d)

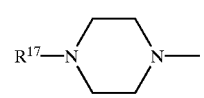

(e)

wherein:
$R^9$, $R^{10}$, $R^{11}$ and $R^{12}$ each independently are hydrogen, halo, halomethyl or $C_{1-6}$alkyl;
m is zero, 1, 2, or 3;
$R^{13}$, $R^{14}$, $R^{15}$ and $R^{16}$ each independently are hydrogen, $C_{1-6}$alkyl, aryl or arylcarbonyl; or
$R^{15}$ and $R^{16}$ taken together may form a bivalent radical $C_{4-5}$alkanediyl;
$R^{17}$ is hydrogen, $C_{1-6}$alkyl, $C_{1-6}$alkylcarbonyl, halomethylcarbonyl, $C_{1-6}$alkyloxycarbonyl, aryl, di(aryl)methyl or $C_{1-6}$alkyl substituted with hydroxy, $C_{1-6}$alkyloxy, carboxyl, $C_{1-6}$alkylcarbonyloxy, $C_{1-6}$alkyloxycarbonyl or aryl;
$R^3$ and $R^4$ are both halogen; or
$R^3$ is halogen and $R^4$ is hydrogen; or
$R^3$ is hydrogen and $R^4$ is halogen; and
aryl is phenyl or phenyl substituted with 1, 2 or 3 substituents selected from halo, hydroxy, $C_{1-6}$alkyl and halomethyl.

In the foregoing definitions $C_{1-6}$alkyl defines straight and branch chained saturated hydrocarbon radicals having from 1 to 6 carbon atoms such as, for example, methyl, ethyl, propyl, butyl, 1-methylpropyl, 1,1-dimethylethyl, pentyl, hexyl; $C_{4-5}$alkanediyl defines bivalent straight and branch chained saturated hydrocarbon radicals having from 4 to 5 carbon atoms such as, for example, 1,4-butanediyl, 1,5-pentanediyl; halo is generic to fluoro, chloro, bromo and iodo. The term halomethyl is meant to include mono-, di-, and trihalomethyl. Examples of halomethyl are fluoromethyl, difluoromethyl and particularly trifluoromethyl.

The pharmaceutically acceptable addition salts as mentioned hereinabove are meant to comprise the therapeutically active non-toxic base and acid addition salt forms which the compounds of formula (I) are able to form. The acid addition salt form of a compound of formula (I) that occurs in its free form as a base can be obtained by treating the free base form of the compound of formula (I) with an appropriate acid such as an inorganic acid, for example, hydrohalic acid, e.g. hydrochloric or hydrobromic, sulfuric, nitric, phosphoric and the like acids; or an organic acid, such as, for example, acetic, hydroxyacetic, propanoic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Particular acid addition salts include hydrochloric acid and [R-(R*,R*)]-2,3-dihydroxy-butanedioic acid (other names are for instance tartaric acid, d-tartaric acid and L-tartaric acid).

The compounds of formula (I) containing acidic protons may be converted into their therapeutically active non-toxic base, i.e. metal or amine, addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like. Conversely said salt forms can be converted into the free forms by treatment with an appropriate base or acid.

The term addition salt as used hereinabove also comprises the solvates which the compounds of formula (I) as well as the salts thereof, are able to form. Such solvates are for example hydrates, alcoholates and the like.

The N-oxide forms of the compounds of formula (I) are meant to comprise those compounds of formula (I) wherein one or several nitrogen atoms are oxidized to the so-called N-oxide, particularly those N-oxides wherein the nitrogen bearing the $R^1$ and $R^2$ substituents is N-oxidized.

The term "stereochemically isomeric forms" as used hereinbefore and hereinafter defines all the possible stereoisomeric forms in which the compounds of formula (I) may exist, thus, also including enantiomers, enantiomeric mixtures and diastereomeric mixtures. Unless otherwise mentioned or indicated, the chemical designation of compounds denotes the mixture, and in particular the racemic mixture, of all possible stereochemically isomeric forms, said mixtures containing all diastereomers and enantiomers of the basic molecular structure. The same applies to the intermediates as described herein, used to prepare endproducts of formula (I). Stereochemically isomeric forms of the compounds of formula (I) and mixtures of such forms are intended to be encompassed by formula (I).

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure compounds or intermediates' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' or equivalent terms should be understood in a similar way, but then having regard to the enantiomeric excess, respectively the diastereomeric excess of the mixture in question.

The numbering of the tetracyclic ring-system present in the compounds of formula (I), as defined by Chemical Abstracts nomenclature is shown in formula (I').

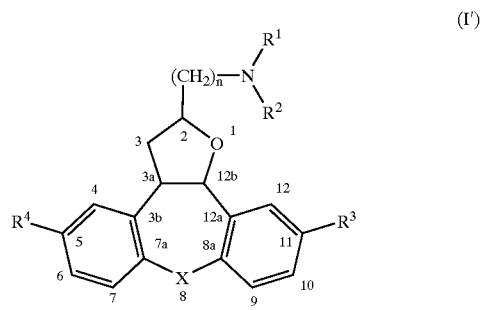

The compounds of formula (I) have at least three asymmetric centers, namely carbon atom 2, carbon atom 3a and carbon atom 12b. Carbon atoms 3a and 12b are part of an annelated ring system. In this case, where more than 2 asymmetric carbon atoms are present on a ring system, the substituent highest in priority (according to the Cahn-Ingold-Prelog sequence rules) on the reference carbon atom, which is defined as the asymmetric carbon atom having the lowest ring number, is arbitrarily always in the "α" position of the mean plane determined by the ring system. The position of the highest priority substituent on the other asymmetric carbon atoms relative to the position of the highest priority substituent on the reference atom is denominated by "α" or "β". "α" means that the highest priority substituent is on the same side of the mean plane determined by the ring system, and "β" means that the highest priority substituent is on the other side of the mean plane determined by the ring system.

Of some compounds of formula (I) and of intermediates used in their preparation, the absolute stereochemical configuration was not experimentally determined. In those cases the stereochemically isomeric form which was first isolated is designated as "A" and the second as "B", without further reference to the actual stereochemical configuration. However, said "A" and "B" isomeric forms can be unambiguously characterized by for instance their optical rotation in case "A" and "B" have an enantiomeric relationship. A person skilled in the art is able to determine the absolute configuration of such compounds using art-known methods such as, for example, X-ray diffraction.

For example, compound 4 having the stereochemical descriptor A-(2α,3aβ,12bα) denotes the pure enantiomer having either (a) the [2R-(2α,3aβ,12bα)] configuration whereby carbon atom 2 is the reference atom having the R configuration and the —$CH_2$—$N(CH_3)_2$ substituent is on the a-side of the mean plane, carbon atom 3a has the S configuration because the hydrogen substituent is on the other side of the mean plane relative to the —$CH_2$—$N(CH_3)_2$ substituent, and carbon atom 12b has the R configuration because the hydrogen substituent is on the same side of the mean plane relative to the —$CH_2$—$N(CH_3)_2$ substituent, or (b) the [2S-(2α,3aβ,12bα)] configuration whereby carbon atom 2 has the S configuration, carbon atom 3a the R configuration and carbon atom 12b the S configuration.

Whenever used hereinafter, the term "compounds of formula (I)" is meant to also include the pharmaceutically acceptable addition salts, the stereoisomeric forms, and also the N-oxide forms.

A special group of compounds are those compounds of formula (I) wherein the two hydrogen atoms on carbon atom 3a and 12b are on opposite sides of the mean plane determined by the tetracyclic ring system.

Interesting compounds are those compounds of formula (I) wherein $R^1$ and $R^2$ are each independently hydrogen or $C_{1-6}$alkyl, or wherein $R^1$ and $R^2$ are taken together with the nitrogen atom to which they are attached, thus forming a morpholinyl ring or a radical of formula (c) or (e); particularly interesting are those compounds of formula (I) wherein $R^1$ and $R^2$ are each independently hydrogen or methyl; more in particular both $R^1$ and $R^2$ are methyl.

Other interesting compounds are those compounds of formula (I) wherein X is $CH_2$.

Still other interesting compounds are those compounds of formula (I) wherein n is 1, 2 or 3, more specifically, n is 1.

Particular compounds are those compounds of formula (I) wherein $R^3$ is hydrogen and $R^4$ is halo, more specifically fluor.

Other particular compounds are those compounds of formula (I) wherein $R^4$ is hydrogen and $R^3$ is halo, more specifically fluor.

Still other particular compounds are those compounds of formula (I) wherein $R^3$ and $R^4$ are both halo, more specifically, both fluor.

Preferred compounds are those compounds of formula (I) wherein the two hydrogen atoms on carbon atom 3a and 12b are on opposite sides of the mean plane determined by the ring system, n is 1 and $R^1$ and $R^2$ are methyl.

Most preferred are 11-fluoro-3,3a,8,12b-tetrahydro-N,N-dimethyl-2H-dibenzo-[3,4:6,7]cyclohepta[1,2-b]furan-2-methanamine; the stereochemically isomeric forms and the pharmaceutically acceptable addition salts thereof, and the N-oxide forms thereof, more in particular, those stereoisomeric forms wherein the two hydrogen atoms on carbon atom 3a and 12b are on opposite sides of the mean plane determined by the ring system such as for instance (±)-(2α,3aβ,12bα)-11-fluoro-3,3a,8,12b-tetrahydro-N,N-dimethyl-2H-dibenzo-[3,4:6,7]cyclohepta[1,2-b]furan-2-methanamine and (±)-(2α,3aα,12bβ)-11-fluoro-3,3a,8,12b-tetrahydro-N,N-dimethyl-2H-dibenzo-[3,4:6,7]cyclohepta[1,2-b]furan-2-methanamine.

The compounds of formula (I) can generally be prepared by N-alkylating an intermediate of formula (II) with an intermediate of formula (III) wherein W is a suitable leaving group such as halo. In the intermediates (II) and (III), $R^1$ to $R^4$, n and X are as defined in the compounds of formula (I). Said N-alkylation can conveniently be carried out in a reaction-inert solvent such as, for example, methanol, tetrahydrofuran, methylisobutyl ketone, N,N-dimethylformamide or dimethylsulfoxide, and optionally in the presence of a suitable base. Stirring and elevated temperatures, for instance reflux temperature, may enhance the rate of the reaction. Alternatively, said N-alkylation may also be performed using the procedure described by Monkovic et al. (J. Med. Chem. (1973), 16(4), p. 403–407) which involves the use of a pressurised reaction vessel.

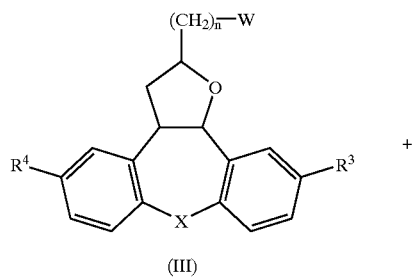

(III)

-continued

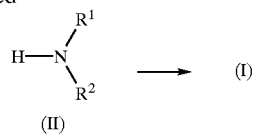

(II)

The compounds of formula (I) may also be converted into each other following art-known transformation reactions.

In addition, the compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g. counter-current distribution, liquid chromatography and the like.

The compounds of formula (I) as prepared in the hereinabove described processes are generally racemic mixtures of enantiomers which can be separated from one another following art-known resolution procedures. The racemic compounds of formula (I) which are sufficiently basic or acidic may be converted into the corresponding diastereomeric salt forms by reaction with a suitable chiral acid respectively with a suitable chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate startng materials, provided that the reaction occurs stereospecifically. Preferably if a specific stereoisomer is desired, said compound will be synthesized by stereospecific methods of preparation. These methods will advantageously employ enantiomerically pure starting materials.

The intermediates mentioned hereinabove are either commercially available or may be made following art-known procedures. For instance, intermediates of formula (IEI) may be prepared according to the procedure described by Monkovic et al. (J. Med. Chem. (1973), 16(4), p. 403–407).

Alternatively, intermediates of formula (III) wherein n is 1, said intermediates being represented by formula (III-a), can also be prepared by reacting an epoxide derivative of formula (IV) with a Grignard reagent of formula (V) wherein Y suitably is halo, thus forming an intermediate of formula (VI) which may subsequently be cyclized according to art-known methods such as the one described in Monkovic et al.

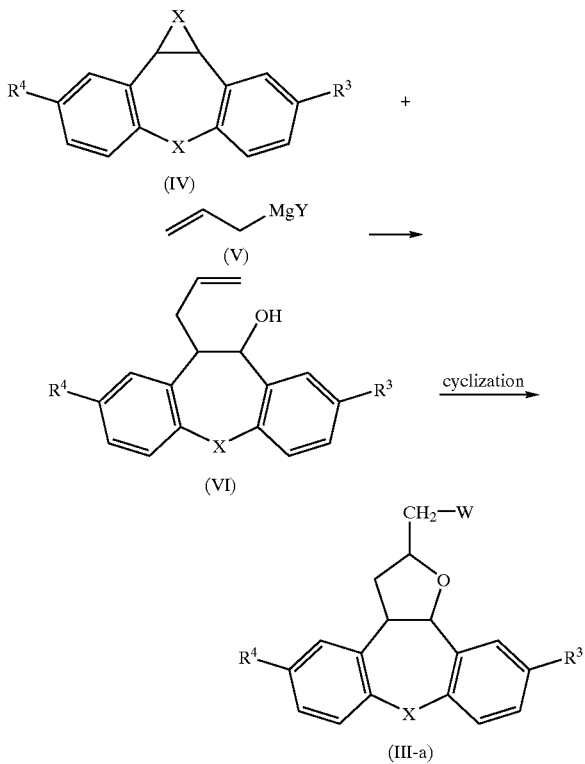

Epoxides of formula (IV) can be prepared using art-known procedures such as peroxidating an intermediate of formula (VHI) with a suitable peroxide such as m-chloroperbenzoic acid.

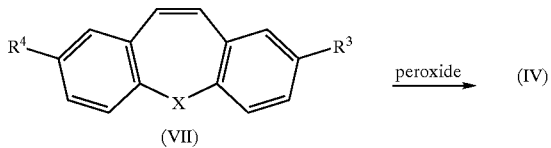

The compounds of the present invention show affinity for 5-HT$_2$ receptors, particularly for 5-HT$_{2A}$ and 5-HT$_{2C}$ receptors (nomenclature as described by D. Hoyer in "Serotonin (5-HT) in neurologic and psychiatric disorders" edited by M. D. Ferrari and published in 1994 by the Boerhaave Commission of the University of Leiden). The serotonin antagonistic properties of the present compounds may be demonstrated by their inhibitory effect in the "5-hydroxytryptophan Test on Rats" which is described in Drug Dev. Res., 13, 237–244 (1988). Furthermore, the compounds of the present invention show interesting pharmacological activity in the "mCPP Test on Rats" which is described hereinafter, and in the "Combined Apomorphine, Tryptamine, Norepinephrine (ATN) Test on Rats" which is described in Arch. Int. Pharmacodyn, 227, 238–253 (1977).

The compounds of the present invention have favourable physicochemical properties. For instance, they are chemically stable compounds, in particular when compared to the compounds disclosed in WO 96/14320 and WO 96/14321. The compounds of the present invention also have a fast onset of action.

In view of these pharmacological and physicochemical properties, the compounds of formula (I) are useful as therapeutic agents in the treatment or the prevention of central nervous system disorders like anxiety, depression and mild depression, bipolar disorders, sleep- and sexual disorders, psychosis, borderline psychosis, schizophrenia, migraine, personality disorders or obsessive-compulsive disorders, social phobias or panic attacks, organic mental disorders, mental disorders in children, aggression, memory disorders and attitude disorders in older people, addiction, obesity, bulimia and similar disorders. In particular, the present compounds may be used as anxiolytics, antipsychotics, antidepressants, anti-migraine agents and as agents having the potential to overrule the addictive properties of drugs of abuse.

The compounds of formula (I) may also be used as therapeutic agents in the treatment of motoric disorders. It may be advantageous to use the present compounds in combination with classical therapeutic agents for such disorders.

The compounds of formula (I) may also serve in the treatment or the prevention of damage to the nervous system caused by trauma, stroke, neurodegenerative illnesses and the like; cardiovascular disorders like high blood pressure, thrombosis, stroke, and the like; and gastrointestinal disorders like dysfunction of the motility of the gastrointestinal system and the like.

In view of the above uses of the compounds of formula (I), it follows that the present invention also provides a method of treating warm-blooded animals suffering from such diseases, said method comprising the systemic administration of a therapeutic amount of a compound of formula (I) effective in treating the above described disorders, in particular, in treating anxiety, psychosis, schizophrenia, depression, migraine, sleep disorders and addictive properties of drugs of abuse.

The present invention thus also relates to compounds of formula (I) as defined hereinabove for use as a medicine, in particular, the compounds of formula (I) may be used for the manufacture of a medicament for treating anxiety, psychosis, schizophrenia, depression, migraine, sleep disorders and addictive properties of drugs of abuse.

Those of skill in the treatment of such diseases could determine the effective therapeutic daily amount from the test results presented hereinafter. An effective therapeutic daily amount would be from about 0.01 mg/kg to about 10 mg/kg body weight, more preferably from about 0.05 mg/kg to about 1 mg/kg body weight.

For ease of administration, the subject compounds may be formulated into various pharmaceutical forms for administration purposes. To prepare the pharmaceutical compositions of this invention, a therapeutically effective amount of the particular compound, optionally in addition salt form, as the active ingredient-is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing compounds of formula (I) may be formulated in an oil for prolonged action. Appropriate oils for this purpose are, for example, peanut oil, sesame oil, cottonseed oil, corn oil, soy bean oil, synthetic glycerol esters of long chain fatty acids and mixtures of these and other oils. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. Acid or base addition salts of compounds of formula (I) due to their increased water solubility over the corresponding base or acid form, are more suitable in the preparation of aqueous compositions.

In order to enhance the solubility and/or the stability of the compounds of formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin. Also co-solvents such as alcohols may improve the solubility and/or the stability of the compounds of formula (I) in pharmaceutical compositions.

Other convenient ways to enhance the solubility of the compounds of the present invention in pharmaceutical compositions are described in WO 97/44014.

More in particular, the present compounds may be formulated in a pharmaceutical composition comprising a therapeutically effective amount of particles consisting of a solid dispersion comprising (a) a compound of formula (I), and
(b) one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermo-dynamics, such a solid dispersion is referred to as "a solid solution". Solid solutions are preferred physical systems because the components therein are usually readily bioavailable to the organisms to which they are administered.

The term "a solid dispersion" also comprises dispersions which are less homogenous throughout than solid solutions. Such dispersions are not chemically and physically uniform throughout or comprise more than one phase.

The water-soluble polymer in the particles is a polymer that has an apparent viscosity of 1 to 100 mPa·s when dissolved in a 2% aqueous solution at 20° C. solution.

Preferred water-soluble polymers are hydroxypropyl methylcelluloses or HPMC. HPMC having a methoxy degree of substitution from about 0.8 to about 2.5 and a hydroxypropyl molar substitution from about 0.05 to about 3.0 are generally water-soluble. Methoxy degree of substitution refers to the average number of methyl ether groups present per anhydroglucose unit of the cellulose molecule. Hydroxy-propyl molar substitution refers to the average number of moles of propylene oxide which have reacted with each anhydroglucose unit of the cellulose molecule.

The particles as defined hereinabove can be prepared by first preparing a solid dispersion of the components, and then optionally grinding or milling that dispersion. Various techniques exist for preparing solid dispersions including melt-extrusion, spray-drying and solution-evaporation, melt-extrusion being preferred.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The following examples are intended to illustrate and not to limit the scope of the present invention.

Experimental Part

A. Preparation of the Intermediate Compounds

EXAMPLE A.1 a) LiAlH$_4$ (0.0686 mol) was added dropwise to a suspension of AlCl$_3$ (0.0718 mol) in tetrahydrofuran (75 ml), cooled on an ice-bath and under N$_2$ atmosphere. The mixture was stirred for 10 minutes at 0° C. A solution of 2-fluoro-5H-dibenzo[a,d]cyclohepten-5-one (0.0653 mol and prepared as described in DE 3,644,462) in tetrahydrofuran (75 ml) was added dropwise and the resulting reaction mixture was allowed to warm to room temperature. Then, the reaction mixture was stirred and refluxed for 2 hours. The mixture was cooled on an ice-bath. Water and CH$_2$Cl$_2$ was added. The organic layer was washed with a saturated aqueous NaHCO$_3$ solution, dried, filtered and the solvent was evaporated, yielding 13.16 g (96%) of 2-fluoro-5H-dibenzo[a.d]cycloheptene (intermediate 1)

b) Metachloroperbenzoic acid (0.0501 mol) was dissolved in CHCl$_3$ (40 ml). The organic solution was dried, filtered and the filtrate was added dropwise to a solution of intermediate 1 (0.0417 mol) and 1,4-benzenediol (0.26 g) in CHCl$_3$ (70 ml), stirred at 60° C. The reaction mixture was stirred for 2.5 hours at 60° C., then cooled on an ice-bath, washed with a 10% aqueous Na$_2$CO$_3$ solution and brine, dried, filtered and the filtrate was evaporated, yielding 10.42 g of 3-fluoro-6,10b-dihydro-1aH-dibenzo-[3,4:6,7] cyclohept[1,2-b]oxirene (intermediate 2)

c) Bromo-2-propenyl-magnesium (0.0542 mol) was added dropwise to a solution of intermediate 2 (0.04956 mol) in tetrahydrofuran(120 ml) under N$_2$ atmosphere. The reaction mixture was stirred for 30 minutes at room temperature, then stirred and refluxed for 2 hours. The reaction mixture was cooled on an ice-bath, quenched with a 20% NH$_4$Cl solution, and extracted with ethylacetate. The organic layer was separated, dried, filtered and the solvent was evaporated. The residue was purified and separated into two regio-isomers by HPLC over silica gel (eluent: hexanes/ ethylacetate 9/1). Two pure fraction groups were collected and their solvent was evaporated, yielding 4.79 g (36%) of (±)-trans-8-fluoro-10,11-dihydro-11-(2-propenyl)-5H-dibenzo[a,d]cyclohepten-10-ol (intermediate 3) and 2.52 g (19%) of (trans)-2-fluoro-10,11-dihydro-11-(2-propenyl)-5H-dibenzo[a,d]cyclohepten-10ol (intermediate 4).

d) Pyridinium tribromide (0.0175 mol) was added portionwise to a solution of intermediate 3 (0.0175 mol) in $CHCl_3$ (80 ml), cooled on an ice-bath. The reaction mixture was stirred for one hour at room temperature. Water was added. The mixture was stirred for 5 min. The organic layer was separated, washed with water, dried, filtered and the solvent was evaporated. The residue was purified by short column chromatography over silica gel (eluent: hexanes/$CH_2Cl_2$ 4:1, then 1:1). The pure fractions were collected and the solvent was evaporated, yielding 5.02 g (83%) of (±)-[(2α,3aβ,12bα)+(2α,3aα,12β)]-2-(bromomethyl)-11-fluoro-3,3a,8,12b-tetrahydro-2H-dibenzo-[3,4:6,7]-cyclohepta[1,2-b]furan (intermediate 5). In a similar way is prepared (±)-[(2α,3aβ,12bα)+(2α,3aα,12bβ)]-2-(bromomethyl)-5-fluoro-3,3a,8,12b-tetrahydro-2H-dibenzo-[3,4:6,7]-cyclohepta[1,2-b]furan (intermediate 6).

Analogous to intermediate 6, the following intermediates were also prepared: (2α,3aβ,12bα)-2-(bromomethyl)-5-fluoro-3,3a,8,12b-tetrahydro-2H-dibenzo1[3,4:6,7]cyclohepta[1,2-b]furan (intermediate 7); and [(2α,3aβ,12bα)+(2α,3aα,12bβ)]-2-(bromomethyl)-5,11-difluoro-3,3a,8,12b-tetrahydro-2H-dibenzo[3,4:6,7]cyclohepta[1,2-b]furan (intermediate 8).

B. Preparation of the Compounds of Formula (I)

EXAMPLE B.1 a) N,N-dimethylamine (gas) was allowed to bubble through a mixture of intermediate 5 (0.0145 mol) and CaO (5.28 g) in tetrahydrofuran (100 ml) during 8 minutes. The reaction mixture was stirred in a Parr reactor for 16 hours at 125° C. The mixture was allowed to cool to room temperature. The solid was filtered off and the filtrate was evaporated. The residue was washed in a saturated aqueous $NaHCO_3$ solution, then extracted with $CH_2Cl_2$. The organic layer was separated, dried, filtered and the solvent was evaporated. The residue was purified by short open column chromatography over silica gel (eluent: $CH_2Cl_2$/($CH_3OH$/$NH_3$) 98/2). The desired fractions were collected and the solvent was evaporated, yielding (±)-[(2α,3aβ,12bα)+(2α,3aα,12bβ)]-11-fluoro-3,3a,8,12b-tetrahydro-N,N-dimethyl-2H-dibenzo[3,4:6,7]cyclohepta[1,2-b]furan-2-methanamine (compound 1).

b) Compound 1 was dissolved in diethyl ether (20 ml) and converted into the hydrochloric acid salt (1:1) by dropwise addition of 6 N HCl/2-propanol. The solvent was evaporated. The residue was triturated under boiling 2-propanone, filtered off and dried, yielding 2.17 g (43%) of (±)-(2α,3aβ,12bα)-11-fluoro-3,3a,8,12b-tetrahydro N,N-dimethyl-2H-dibenzo[3,4:6,7]cyclohepta[1,2-b]furan-2-methanamine hydrochloride (compound 2; mp. 239. 1° C.).

c) After having repeated the procedures in step a) and b) with more starting material, the solvent of the mother liquor (remaining after having filtered off compound 2) was evaporated. The residue was purified by HPLC over RP-18 (eluent: (0.5% ammonium acetate in $H_2O$)/$CH_3OH$/$CH_3CN$ gradient elution). The pure fractions were collected and the solvent was evaporated, yielding 0.400 g of (±)-(2α,3aα,12bβ)-11-fluoro-3,3a,8,12b-tetrahydro-N,N-dimethyl-2H-dibenzo[3,4:6,7]cyclohepta[1,2-b]furan-2-methanamine (compound 3).

EXAMPLE B.2 a) Compound 2 (0.005 mol) was converted into the free base by treatment with aqueous $NH_4OH$ and extraction with $CH_2Cl_2$. The separated organic layer was dried, filtered and the solvent was evaporated. The free-base residue was separated into its enantiomers by chiral column chromatography over Chiralcel OJ (eluent: hexane/ethanol 90/10). Two pure fraction groups were collected and their solvent was evaporated, yielding 0.702 g (45%) A-(2α,3aβ,12bα)-11-fluoro-3,3a,8,12b-tetrahydro-N,N-dimethyl-2H-dibenzo[3,4:6,7]cyclohepta[1,2-b]furan-2-methanamine (compound 4) and 0.670 g (43%) B-(2α,3aβ,12bα)-11-fluoro-3,3a,8,12b-tetrahydro-N,N-dimethyl-2H-dibenzo[3,4:6,7]cyclohepta[1,2-b]furan-2-methanamine (compound 5).

Analogously, compound 3 was separated into A-(2α,3aα,12bβ)-11-fluoro-3,3a,8,12b-tetrahydro-N,N-dimethyl-2H-dibenzo[3,4:6,7]cyclohepta[1,2-b]furan-2-methanamine (compound 6) and B-(2α,3aα,12bβ)-11-fluoro-3,3a,8,12b-tetrahydro-N,N-dimethyl-2H-dibenzo[3,4:6,7]cyclohepta[1,2-b]furan-2-methanamine (compound 7).

b) Compound 5 (0.0584 mol) was stirred in ethanol (280 ml) at room temperature. A solution of L-tartaric acid (0.0584 mol) in ethanol (50 ml) (dissolved by heating) was added at room temperature and the mixture was stirred for 4 hours at room temperature. The precipitate was filtered off, and dried (vacuum, 40° C., 16 hours), yielding 19.1 g (71%) of [B-(2α,3aβ,12bα)]-11-fluoro-3,3a,8,12b-tetrahydro-N,N-dimethyl-2H-dibenzo[3,4:6,7]cyclohepta[1,2-b]furan-2-methanamine (+)-[R-R*,R*)]-2,3-dihydroxybutanedioate (1:1) (compound 11).

EXAMPLE B.3

A mixture of intermediate 5 (0.0030 mol) and morpholine (0.0075 mol) was stirred for 3 hours at 100° C., then cooled to room temperature and more morpholine (0.0075 mol) was added and the reaction mixture was stirred for one hour at 100° C., then cooled to room temperature and treated with $CH_2Cl_2$. The precipitate was filtered off and the filtrate was evaporated. The resultant oil was purified by short open column chromatography over silica gel (eluent: $CH_2Cl_2$/$CH_3OH_{98/2}$). The pure fractions were collected and the solvent was evaporated. The residue was dissolved in diethyl ether and converted into the hydrochloric acid salt (1:1). The precipitate was filtered off and dried, yielding 0.82 g (70%) of [(2α,3aβ,12bα)+(2α,3aα,12b β)]-11-fluoro-3,3a,8,12b-tetrahydro-2-(4morpholinylmethyl)-2H-dibenzo[3,4:6,7]cyclohepta[1,2-b]furan hydrochloride (compound 19; mp. 281.1° C.).

Table 1 lists compounds of formula (I) which were prepared analogously to one of the above described procedures.

TABLE 1

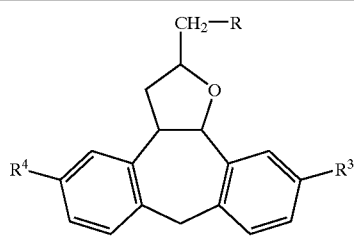

| Co. No. | Ex. No. | $R^3$ | $R^4$ | R | stereochemistry | salt form | melting point |
|---|---|---|---|---|---|---|---|
| 1 | B1a | F | H | $N(CH_3)_2$ | (2α, 3aβ, 12bα) + | free base | |

TABLE 1-continued

[Structure: tetracyclic compound with CH₂—R on furan ring, R⁴ and R³ substituents on aromatic rings]

| Co. No. | Ex. No. | R³ | R⁴ | R | stereo-chemistry | salt form | melting point |
|---|---|---|---|---|---|---|---|
| 2 | B1b | F | H | N(CH₃)₂ | (2α, 3aβ, 12bα) | HCl (1:1) | 239.1° C. |
| 3 | B1c | F | H | N(CH₃)₂ | (2α, 3aα, 12bβ) | free base | |
| 4 | B2a | F | H | N(CH₃)₂ | A-(2α, 3aβ, 12bα) | free base | |
| 5 | B2a | F | H | N(CH₃)₂ | B-(2α, 3aβ, 12bα) | free base | |
| 6 | B2a | F | H | N(CH₃)₂ | A-(2α, 3aα, 12bβ) | free base | |
| 7 | B2a | F | H | N(CH₃)₂ | B-(2α, 3aα, 12bβ) | free base | |
| 8 | B2b | F | H | N(CH₃)₂ | A-(2α, 3aβ, 12bα) | HCl (1:1) | |
| 9 | B2b | F | H | N(CH₃)₂ | A-(2α, 3aβ, 12bα) | L-tartrate (1:1) | |
| 10 | B2b | F | H | N(CH₃)₂ | B-(2α, 3aβ, 12bα) | HCl (1:1) | |
| 11 | B2b | F | H | N(CH₃)₂ | B-(2α, 3aβ, 12bα) | L-tartrate (1:1) | |
| 12 | B2b | F | H | N(CH₃)₂ | A-(2α, 3aα, 12bβ) | L-tartrate (1:1) | |
| 13 | B2b | F | H | N(CH₃)₂ | B-(2α, 3aα, 12bβ) | L-tartrate (1:1) | |
| 14 | B1a | F | F | N(CH₃)₂ | (2α, 3aβ, 12bα) | HCl (1:1) | 256° C. |
| 15 | B2a | F | F | N(CH₃)₂ | A-(2α, 3aβ, 12bα) | free base | |
| 16 | B2a | F | F | N(CH₃)₂ | B-(2α, 3aβ, 12bα) | free base | |
| 17 | B1a | H | F | N(CH₃)₂ | (2α, 3aβ, 12bα) | HCl (1:1) | 225.3° C. |
| 18 | B1b | F | H | NHCH₃ | (2α, 3aβ, 12bα) | HCl (1:1) | 211.4° C. |
| 19 | B3 | F | H | 4-morpholin-yl | (2α, 3aβ, 12bα) + (2α, 3aα, 12bβ) | HCl (1:1) | 281.1° C. |
| 20 | B3 | F | H | 4-methyl-1-piperazinyl | (2α, 3aα, 12bβ) | HCl (1:2) | |
| 21 | B3 | F | H | 4-(2-hydroxy-ethyl)-1-piperazinyl | (2α, 3aα, 12bβ) | HCl (1:2) | 260.3° C. |
| 22 | B3 | F | H | 4-(3-chloro-phenyl)-1-piperazinyl | (2α, 3aβ, 12bα) + (2α, 3aα, 12bβ) | HCl (1:1) | 267.4° C. |
| 23 | B3 | F | H | 4-phenyl-1-piperidinyl | (2α, 3aβ, 12bα) + (2α, 3aα, 12bβ) | HBr (1:1) | 225.8° C. |

TABLE 2 hereinunder lists other compounds of formula which are prepared analogously to one of the above described reaction procedures.

[Structure: tricyclic compound with CH₂—R on furan ring, bridging X group, R⁴ and R³ substituents]

| Co. No. | X | R³ | R⁴ | R | stereochemistry |
|---|---|---|---|---|---|
| 24 | O | F | H | N(CH₃)₂ | (2α, 3aβ, 12bα) + (2α, 3aα, 12bβ) |
| 25 | CH₂ | F | H | 4-(2-hydroxyethyl)-1-piperazinyl | (2α, 3aβ, 12bα) + (2α, 3aα, 12bβ) |
| 26 | CH₂ | F | H | 4-methyl-1-piperazinyl | (2α, 3aβ, 12bα) + (2α, 3aα, 12bβ) |

TABLE 2-continued hereinunder lists other compounds of formula which are prepared analogously
to one of the above described reaction procedures.

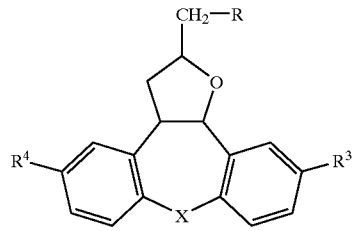

| Co. No. | X | R³ | R⁴ | R | stereochemistry |
|---|---|---|---|---|---|
| 27 | $CH_2$ | F | H | ![piperidinyl-C(=O)-C6H4-F] | (2α, 3aβ, 12bα) + (2α, 3aα, 12bβ) |
| 28 | $CH_2$ | H | F | 4-phenyl-1-piperidinyl | (2α, 3aβ, 12bα) + (2α, 3aα, 12bβ) |
| 29 | $CH_2$ | H | F | ![piperidinyl-C(=O)-C6H4-F] | (2α, 3aβ, 12bα) + (2α, 3aα, 12bβ) |
| 30 | $CH_2$ | H | F | 4-morpholinyl | (2α, 3aβ, 12bα) + (2α, 3aα, 12bβ) |
| 31 | O | F | F | $N(CH_3)_2$ | (2α, 3aβ, 12bα) + (2α, 3aα, 12bβ) |
| 32 | $CH_2$ | F | F | 4-(2-hydroxyethyl)-1-piperazinyl | (2α, 3aβ, 12bα) + (2α, 3aα, 12bβ) |
| 33 | $CH_2$ | F | F | 4-methyl-1-piperazinyl | (2α, 3aβ, 12bα) + (2α, 3aα, 12bβ) |

C. Pharmacological Example

EXAMPLE C.1
"mCPP Test on Rats"

Rats were treated with the test compound at a varying dose at a pre-test time T of 1 hour and with 1 mg/kg mCPP (metachlorophenylpiperazine), injected intravenously, 15 minutes prior to the test. After pre-test time T elapsed, treated rats were submitted to the "Open Field Test on Rats" as described in Drug Dev. Res. 18, 119–144 (1989), but using an infra-red light source instead of a Kleverlux® (12V/20W) light source. A dose at which 40% or more of the tested rats showed suppression of the mCPP induced effects, i.e. mCPP-antagonism, was defined as an active dose. Compound numbers 2 and 8 through 16 were active at a test dose of 2.5 mg/kg or lower. Other compounds were either not tested or were active at a higher dose.

Complete antagonism of the mCPP induced effects, meaning that 100% of the tested rats showed complete suppression of the mCPP induced effects, was observed for compound numbers 2 and 10 at a dose of 2.5 mg/kg or less.

In order to test the fast onset of action of a test compound in reversing the mCPP induced effects, the above experiment was repeated whereby rats were treated intravenously with mCPP at a pre-test time T of 15 minutes, and intravenously with the test compound at varying doses at a pre-test time T of 5 minutes.

Compound numbers 2, 8, 9, 10, 11 and 12 were active at a test dose of 2.5 mg/kg or lower and thus proved to have a fast onset of action.

EXAMPLE C.2

"Apomorphine, Tryptamine, Norepinephrine (ATN) Test in Rats"

The antipsychotic activity of the subject compounds is evidenced by the experimental data obtained in the combined apomorphine (APO), tryptamine (TRY) and norepinephrine (NOR) test in rats. Said combined apomorphine, tryptamine and norepinephrine test is described in Arch. Int. Pharmacodyn., 227, 238–253 (1977) and provides an empirical evaluation of the relative specificity with which drugs may effect particular neurotransmitter systems centrally (CNS) as well as peripherally. In particular, the test demonstrates the antagonistic activity of the tested compounds of formula (I) on dopamine (by preventing the symptoms elicited with the dopamine agonist apomorphine such as, for example, agitation and stereotypy), on serotonin (by preventing the central symptoms elicited with the serotonin agonist tryptamine such as, for example, bilateral clonic convulsions, tremors and backward locomotion, and peripheral symptoms such as for example cyanosis), and on norepinephrine (by preventing or delaying death upon administration of the a-agonist norepinephrine). The favourable pharmacological property of the present compounds compared to the compounds specifically disclosed in WO 97/38991 lies in their ability to antagonize the central symptoms elicited by apomorphine and tryptamine.

TABLE 3 compares the ED$_{50}$ values in mg/kg (effective dose at which the induced symptoms are antagonized in 50% of the tested rats) for present compound numbers 9, 11, 12 and 13 with the following compounds as disclosed in WO 97/38991:

![structure]

| Compound | stereochemistry | salt form |
|---|---|---|
| a | A-(2α, 3aβ, 12bα) | L-tartrate (1:1) H$_2$O (1:1) |
| b | B-(2α, 3aβ, 12bα) | S-malic acid (1:1) |
| c | A-(2α, 3aα, 12bβ) | L-tartrate (1:1) |
| d | B-(2α, 3aα, 12bβ) | S-malic acid (1:1) |

The observations to determine whether or not a test compound did antagonize the centrally induced symptoms were performed for apomorphine antagonism at 30 minutes and for tryptamine antagonism at 90 minutes following subcutaneous administration of test compound.

TABLE 3

| Present invention | | WO 97/38991 | |
|---|---|---|---|
| Comp. No. | ED$_{50}$ (mg/kg) | Compound | ED$_{50}$ (mg/kg) |
| Apomorphine interaction | | | |
| Antagonism of agitation and stereotypy | | | |
| 9 | 2.0 | a | >10 |
| 11 | 2.0 | b | >10 |
| 12 | 10 | c | >10 |
| 13 | 0.2 | d | 2.7 |
| Tryptamine interaction | | | |
| Antagonism of bilateral clonic convulsions | | | |
| 9 | 0.7 | a | ≧10 |
| 11 | 0.4 | b | 1.3 |
| 12 | 5 | c | 1.25 |
| 13 | 0.07 | d | 0.15 |
| Antagonism of backward locomotion | | | |
| 9 | 1.4 | a | 10 |
| 11 | 0.5 | b | 1.3 |
| 12 | 5 | c | 10 |
| 13 | 0.06 | d | 0.2 |

D. Composition Examples

"Active ingredient"(A.I.) as used throughout these examples relates to a compound of formula (I), a pharmaceutically acceptable acid addition salt, a stereochemically isomerec form thereof or a N-oxide form thereof.

EXAMPLE D.1
Oral Solution

Methyl 4-hydroxybenzoate (9 g) and propyl 4-hydroxybenzoate (1 g) were dissolved in boiling purified water (4 l). In 3 l of this solution were dissolved first 2,3dihydroxybutanedioic acid ( 10 g) and thereafter A.I (20 g). The latter solution was combined with the remaining part of the former solution and 1,2,3-propanetriol (12 l) and sorbitol 70% solution (3 l) were added thereto. Sodium saccharin (40 g) were dissolved in water (500 ml) and raspberry (2 ml) and gooseberry essence (2 ml) were added. The latter solution was combined with the former, water was added q.s. to a volume of 20 l providing an oral solution comprising 5 mg of the active ingredient per teaspoonful (5 ml). The resulting solution was filled in suitable containers.

EXAMPLE D.2
Film-Coated Tablets
Preparation of Tablet Core

A mixture of A.I. (100 g), lactose (570 g) and starch (200 g) was mixed well and thereafter humidified with a solution of sodium dodecyl sulfate (5 g) and polyvinylpyrrolidone (10 g) in water (200 ml). The wet powder mixture was sieved, dried and sieved again. Then there was added microcrystalline cellulose (100 g) and hydrogenated vegetable oil (15 g). The whole was mixed well and compressed into tablets, giving 10.000 tablets, each containing 10 mg of the active ingredient.

Coating

To a solution of methyl cellulose (10 g) in denaturated ethanol (75 ml) there was added a solution of ethyl cellulose (5 g) in dichloromethane (150 ml). Then there were added dichloromethane (75 ml) and 1,2,3-propanetriol (2.5 ml). Polyethylene glycol (10 g) was molten and dissolved in dichloromethane (75 ml). The latter solution was added to the former and then there were added magnesium octadecanoate (2.5 g), polyvinylpyrrolidone (5 g) and concentrated colour suspension (30 ml) and the whole was homogenated. The tablet cores were coated with the thus obtained mixture in a coating apparatus.

EXAMPLE D.3
Injectable Solution

Methyl 4-hydroxybenzoate (1.8 g) and propyl 4-hydroxybenzoate (0.2 g) were dissolved in boiling water (500 ml) for injection. After cooling to about 50° C. there were added while stirring lactic acid (4 g), propylene glycol (0.05 g) and A.I. (4 g). The solution was cooled to room temperature and supplemented with water for injection q.s. ad 1000 ml, giving a solution comprising 4 mg/ml of A.I.. The solution was sterilized by filtration and filled in sterile containers.

What is claimed is:
1. A compound of formula

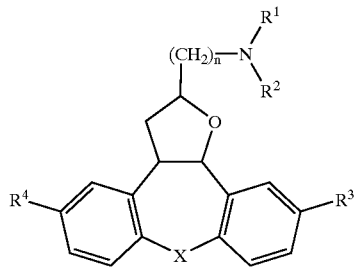

(I)

a N-oxide form, a pharmaceutically acceptable addition salt or a stereochemically isomeric form thereof, wherein:
n is zero, 1, 2, 3, 4, 5 or 6;
X is CH$_2$ or O;
R$^1$ and R$^2$ each independently are hydrogen, C$_{1-6}$alkyl, C$_{1-6}$alkylcarbonyl, halomethylcarbonyl or C$_{1-6}$alkyl substituted with hydroxy, C$_{1-6}$alkyloxy, carboxyl, C$_{1-6}$alkylcarbonyloxy, C$_{1-6}$alkyloxycarbonyl or aryl; or
R$^1$ and R$^2$ taken together with the nitrogen atom to which they are attached may form a morpholinyl ring or a radical of formula:

(a) 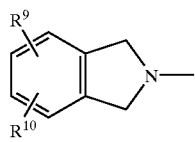

(b) 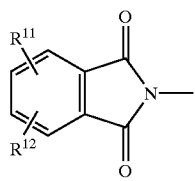

(c) 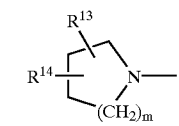

(d) 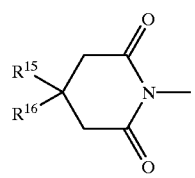

(e) 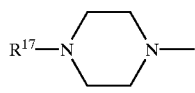

wherein:
$R^9$, $R^{10}$, $R^{11}$ and $R^{12}$ each independently are hydrogen, halo, halomethyl or $C_{1-6}$alkyl;
m is zero, 1, 2, or 3;
$R^{13}$, $R^{14}$, $R^{15}$ and $R^{16}$ each independently are hydrogen, $C_{1-6}$alkyl, aryl or arylcarbonyl; or
$R^{15}$ and $R^{16}$ taken together may form a bivalent radical $C_{4-5}$alkanediyl;

$R^{17}$ is hydrogen, $C_{1-6}$alkyl, $C_{1-6}$alkylcarbonyl, halomethylcarbonyl, $C_{1-6}$alkyloxycarbonyl, aryl, di(aryl)methyl or $C_{1-6}$alkyl substituted with hydroxy, $C_{1-6}$alkyloxy, carboxyl, $C_{1-6}$alkylcarbonyloxy, $C_{1-6}$alkyloxycarbonyl or aryl;
$R^3$ and $R^4$ are both fluoro; or
$R^3$ is fluoro and $R^4$ is hydrogen; or
$R^3$ is hydrogen and $R^4$ is fluoro; and
aryl is phenyl or phenyl substituted with 1, 2 or 3 substituents selected from halo, hydroxy, $C_{1-6}$alkyl and halomethyl.

2. A compound as claimed in claim 1 wherein X is $CH_2$.

3. A compound as claimed in claim 1 wherein the hydrogen atoms on carbon atoms 3a and 12b are on opposite sides of the mean plane determined by the tetracyclic ring system.

4. A compound as claimed in any one of claims 1 to 3 wherein $R^3$ is fluoro and $R^4$ is hydrogen.

5. A compound as claimed in claim 1 wherein n is 1.

6. A compound as claimed in claim 1 wherein both $R^1$ and $R^2$ are each independently selected from hydrogen or $C_{1-6}$alkyl or when taken together with the nitrogen atom to which they are attached form a morpholinyl ring or radical of formula (c) or (e).

7. A compound as claimed in claim 1 wherein the compound is 11-fluoro-3,3a,8,12b-tetrahydro-N,N-dimethyl-2H-dibenzo-[3,4:6,7]cyclohepta[1,2-b]furan-2-methanamine; a stereochemically isomeric form or a pharmaceutically acceptable addition salt thereof, or a N-oxide form thereof.

8. A composition comprising a pharmaceutically acceptable carrier and, as active ingredient, a therapeutically effective amount of a compound as claimed in claim 1.

9. A method for treating a disorder selected from the group consisting of anxiety, psychosis, schizophrenia, depression, migraine, sleep disorders and drug addiction in a warm-blooded animal in need thereof, comprising administering to the warm-blooded animal a therapeutically effective amount of the compound of claim 1.

* * * * *